(12) United States Patent
Walzman

(10) Patent No.: US 12,089,851 B2
(45) Date of Patent: *Sep. 17, 2024

(54) MICROCATHETERS FOR INJECTING EMBOLIC LIQUID AGENTS INTO VESSELS

(71) Applicant: Daniel Ezra Walzman, Bergenfield, NJ (US)

(72) Inventor: Daniel Ezra Walzman, Bergenfield, NJ (US)

( * ) Notice: Subject to any disclaimer, the term of this patent is extended or adjusted under 35 U.S.C. 154(b) by 941 days.

This patent is subject to a terminal disclaimer.

(21) Appl. No.: 17/078,521

(22) Filed: Oct. 23, 2020

(65) Prior Publication Data

US 2021/0038231 A1    Feb. 11, 2021

Related U.S. Application Data

(63) Continuation-in-part of application No. 16/779,548, filed on Jan. 31, 2020, which is a continuation-in-part of application No. 15/731,804, filed on Aug. 3, 2017, now Pat. No. 10,575,856.

(60) Provisional application No. 62/600,137, filed on Feb. 13, 2017.

(51) Int. Cl.
*A61B 17/12* (2006.01)
*A61M 25/00* (2006.01)

(52) U.S. Cl.
CPC .. *A61B 17/12186* (2013.01); *A61B 17/12109* (2013.01); *A61M 25/007* (2013.01); *A61M 25/0075* (2013.01); *A61M 2025/0042* (2013.01)

(58) Field of Classification Search
CPC ............ A61M 25/007; A61M 25/0075; A61M 25/0074; A61M 2025/0076; A61M 2025/0073; A61M 2025/0018; A61B 17/12181; A61B 17/12159
See application file for complete search history.

(56) References Cited

U.S. PATENT DOCUMENTS

| | | |
|---|---|---|
| 4,755,176 A | 7/1988 | Patel |
| 4,784,638 A | 11/1988 | Ghajar et al. |
| 4,970,926 A | 11/1990 | Ghajar et al. |
| 5,180,387 A | 1/1993 | Ghajar et al. |
| 5,380,276 A | 1/1995 | Miller et al. |
| 5,800,407 A | 9/1998 | Eidor |
| 5,954,687 A | 9/1999 | Baudino |
| 6,223,637 B1 | 5/2001 | Hansen |

(Continued)

OTHER PUBLICATIONS

International search report for international application PCT/US20/62486 mailed Mar. 10, 2021.
European Search Report EP 20917233 Dated: Jan. 25, 2024.

*Primary Examiner* — Scott J Medway
*Assistant Examiner* — Anh Bui
(74) *Attorney, Agent, or Firm* — Neil D. Gershon

(57) ABSTRACT

A device and method for injecting liquid embolic agents utilizing a "plug and push" technique. The device/catheter has at least one side hole or an externally swellable region which creates a plug upstream of the distalmost portion of the catheter and thereby ameliorates the suboptimal outcomes associated with creating a plug upstream of a distal end hole via injecting embolic agents only at the distalmost portion of the catheter. The catheter can include a flow restricting structure to initially block flow of the liquid embolic agent out the distal end hole and direct flow of the liquid embolic agent through the one or more side holes.

19 Claims, 6 Drawing Sheets

(56) References Cited

U.S. PATENT DOCUMENTS

| | | |
|---|---|---|
| 6,569,145 B1 | 5/2003 | Shmulewitz |
| 8,403,911 B2 | 3/2013 | Garrison et al. |
| 8,496,629 B2 | 7/2013 | Mckinnon et al. |
| 9,364,634 B2 | 6/2016 | Adams et al. |
| 9,399,112 B2 | 7/2016 | Shevgoor et al. |
| 9,440,043 B2 | 9/2016 | Arora et al. |
| 10,575,856 B2 * | 3/2020 | Walzman ......... A61B 17/12159 |
| 2007/0073271 A1 | 3/2007 | Brucker |
| 2008/0183128 A1 | 7/2008 | Morriss |
| 2010/0036410 A1 | 2/2010 | Krolik |
| 2010/0049165 A1 * | 2/2010 | Sutherland ....... A61B 17/12109 |
| | | 604/529 |
| 2011/0251545 A1 * | 10/2011 | Duffy ..................... A61L 27/14 |
| | | 604/522 |
| 2013/0310687 A1 | 11/2013 | Takizawa |
| 2014/0039459 A1 | 2/2014 | Folk |
| 2015/0088100 A1 | 3/2015 | Oborn |
| 2015/0119674 A1 | 4/2015 | Fischell et al. |
| 2015/0174381 A1 | 6/2015 | Morita |
| 2015/0209550 A1 | 7/2015 | Teh |
| 2018/0049747 A1 | 2/2018 | Tal et al. |
| 2018/0104443 A1 | 4/2018 | Walzman |
| 2018/0228494 A1 | 8/2018 | Walzman |
| 2019/0001113 A1 | 1/2019 | Call |
| 2019/0329000 A1 | 10/2019 | Tal et al. |
| 2020/0016310 A1 * | 1/2020 | Spears .................. A61M 1/267 |
| 2020/0178982 A1 * | 6/2020 | Walzman ......... A61B 17/12109 |

\* cited by examiner

MICROCATHETERS FOR INJECTING EMBOLIC LIQUID AGENTS INTO VESSELS This application is a continuation in part of application Ser. No. 16/779,548, filed Jan. 31, 2020, which is a continuation in part of application Ser. No. 15/731,804, filed Aug. 3, 2017, U.S. Pat. No. 10,575,856, which claims the benefit of provisional application Ser. No. 62/600,137, filed Feb. 13, 2017. The entire contents of each of these applications are incorporated by reference herein.

BACKGROUND OF THE INVENTION

Field of the Invention

This application relates to catheters for injecting embolic liquid agents into vessel lumens to embolize the vasculature.

Background

Treatment of brain arteriovenous malformations includes endovascular embolization, surgical resection, and stereotactic radiotherapy, alone or in combination. In the past, n-butyl cyanoacrylate (nBCA) was used as an adjunct to surgery, however, introduction of a dimethyl sulfoxide (DMSO)-based embolic agent, Onyx (ev3, Covidien), and more recently in other countries, PHIL™ (Precipitating Hydrophobic Injectable Liquid, MicroVention® Terumo) and SquidPERI (EVOH, by emboflu, Switzerland), and advancement in micro-catheter design often offered better endovascular results in brain arteriovenous malformations treatment. Liquid embolic agents are the preferred embolic material in endovascular treatment of pial and brain arteriovenous malformations and dural arteriovenous fistulas. Advancements in micro-catheter design and emergence of new embolic agents offer better results in endovascular treatment of brain arteriovenous malformations.

Among said advances is the use of dual lumen devices which employ one lumen to dispense a balloon to block Onyx flow and a second lumen to deploy Onyx. The prior art teaches that double-lumen catheters are more efficient than single-lumen catheters because the double-lumen allows simultaneous execution of tasks. However, the addition of a second lumen and a balloon can inhibit the tracking of catheters to a target in small and tortuous vessels.

The prior art contains several catheters with a hole in addition to the end hole, such as U.S. Pat. Nos. 9,440,043 9,399,112; 9,364,634; 8,496,629; 8,403,911; 6,223,637; 5,954,687; 5,800,407; 5,180,387; 4,970,926; 4,784,638; and 4,755,176.

However, most of these catheters are designed to drain cerebrospinal fluid from the ventricular through a catheter that enters through a hole in the skull and would not be capable of injecting glue into an artery that enters through the femoral artery and is snaked up through blood vessels in the body. Additionally, the catheters described in these patents could be used to inject something directly into the brain and/or ventricle. However, they could not be used to inject something into an artery within the brain, or to provide a temporary arterial bypass. If it were introduced directly into the artery through the brain it would undoubtedly cause a life-threatening bleed in the brain. The medical basis is that a catheter designed to be inserted directly into the brain has no possible role for an intravascular application.

Additionally, the structure of the devices taught by the above-listed patents differs from the structure of the present invention. For example, U.S. Pat. No. 9,440,043, discloses a catheter having a tapered structure and balloon formed above a lower drainage hole which covers the distal end hole. U.S. Pat. No. 9,399,112 discloses a catheter hole having an inclined trailing edge, U.S. Pat. No. 9,364,634 discloses an embedded co-extrusion for improving catheter hole array efficiency, U.S. Pat. No. 8,496,629 discloses a catheter using staggered diffusion holes as a flow breaking feature, U.S. Pat. No. 8,403,911 discloses a catheter using diffusion side holes to improve catheter efficiency, U.S. Pat. No. 6,223,637 discloses a catheter sidewall hole cutting apparatus, U.S. Pat. No. 5,954,687 discloses a catheter having a fluid reservoir, and U.S. Pat. No. 5,800,407 discloses a multiple hole epidural catheter which uses both permanently opened and permanently closed holes. Furthermore, the present invention is designed for intravascular, not epidural use. U.S. Pat. No. 5,180,387 teaches the use of angled holes in a catheter with a non-circular bore.

U.S. Pat. No. 4,970,926 discloses an apparatus for making an angled hole ventricular catheter which uses a plurality of rods with an end hole in each, U.S. Pat. No. 4,784,638 shows an angled hole ventricular catheter designed for extended impartment in the brain. U.S. Pat. No. 4,755,176 discloses a catheter with side hole in one of two lumens.

The use of the "plug and push" technique for injecting liquid embolic agents into a vessel is known to effect occlusion of the vessel. After injection, the agent solidifies to embolize the vasculature. In these techniques, the embolic agent is injected out the distal hole. However, the prior art suffers from several significant shortcomings. These include difficulty forming a proximal "plug" before too much distal embolic agent, e.g., Onyx, prevents a subsequent ejective distal "push", and too much reflux of the embolic agent along the micro-catheter, approaching a normal branch artery, necessitating aborting that injection for safety concerns. Other shortcomings include slow plug formation, resulting in the need for longer procedures necessitating longer fluoroscopic times and higher radiation doses.

The prior art also fails to adequately address the fact that the initial "plug" injection(s) of embolic agent, such as Onyx 34, (after lacing the micro-catheter with dimethyl sulfoxide) is often off target. Consequently, some of the plug material ends up in the distal most tip of the micro-catheter. Additionally, typically the plugging material, such Onyx 34, when in contact with blood that is not moving will then start to solidify in the tip of the micro-catheter, and can obstruct it. If it becomes obstructed, distal penetration of the lesion being treated with the embolic agent is no longer possible.

These prior art micro-catheters and embolic agents often require creating a plug at the distalmost portion of the micro-catheters in order to facilitate optimal subsequent embolic penetration. Typically, treatments are suboptimal when there is difficulty forming a "plug". The difficulties can result in liquid embolic failure to penetrate the target area, such as a fistula's nidus.

Therefore, the need exists for an improved liquid embolic agent delivery system to ameliorate the above-mentioned shortcomings and difficulties. The need also exists to provide an embolic agent delivery system that is more consistently effective. It would be advantageous to provide such system that is easier to use than existing delivery systems, allows faster plug formation, and requires less procedural time and X-ray/radiation dosage.

SUMMARY OF INVENTION

The present invention overcomes the problems and deficiencies of the prior art.

The present invention provides a device which facilitates creation of a plug or plug-equivalent near but proximal to the distal end hole of the microcatheter, thereby ameliorating current difficulties in creating the plug utilizing embolic agent in the plug and push technique.

The present invention in one aspect provides a single lumen micro-catheter with a single or multiple side holes a set short distance from the end hole (typically between about 5 mm to about 30 mm). The hole positioning is designed to allow the more viscous Onyx 34 (or higher viscosity versions of MicroVention's Precipitating Hydrophobic Injectable Liquid, or similar liquid embolic agents) to be delivered more proximately to a targeted location. This delivery allows the formation of a proximal "plug" more easily.

As a result of such targeted delivery of a "plug", less viscous Onyx 18 (or similar less viscous material) consequently can then be more easily "pushed" into an AVM nidus or another target lesion more effectively. This results in better distal lesion penetration, and less chance of unwanted proximal reflux along the catheter and into another vessel.

Some embodiments of the present invention incorporate valve technology to control the flow of the embolic agent. The valve technology can in some embodiments use semipermeable material to control selected fluids by employing selectively permeable, or non-permeable material to control flow, or a combination thereof. The selective flow control valve embodiment of the current invention can be set with a fixed flow through area. The variable flow control valve embodiment of the present invention allows variable flow control area. The variability of flow area is capable of responding to changes in pressure, fluid viscosity, magnetic field or combinations thereof, or other differential conditions.

Some embodiments of the present invention incorporate differential inner diameter sizing of a catheter, which can be used together with a wire, or together with a detached wire or coil, to allow flow of liquids and/or liquid embolic through the majority of the catheter and out the distal side hole, while preventing unwanted early filling of the distalmost portion of the catheter beyond the side hole.

For example, in some embodiments, the micro-catheter from a proximal portion up to the side hole can have an ID of about 0.014", and beyond the side hole it may have an ID of about 0.007". Once the micro-catheter is in the desired position for embolization, DMSO followed by Onyx 34 (or other more viscous agents) can be injected with a wire in the catheter to create a "plug" at the side hole as the Onyx 34 exits the side hole. The wire completely functionally obstructs the portion (lumen) of the catheter distal to the side hole, which has an ID that can effectively match the OD of the wire, thus preventing Onyx from entering that segment of the catheter before desired, and possibly hardening within that portion of the catheter and obstructing it. Once an adequate "plug" has been formed, the wire can be removed and less viscous Onyx 18 (or similar) can be "pushed" out the distal hole of the catheter and into the target lesion.

Another embodiment of the present invention does not have a side hole. Instead, at a similar location along the distal portion of the catheter, it has a thin layer of hydrogel adhered along the entire circumference of the catheter. The hydrogel can be such that it expands after a certain amount of time exposed to blood, or with a certain electrical magnetic signal, or with infusion of a certain triggering liquid, or other trigger. Once the catheter is in the desired position, the hydrogel can be expanded, and the hydrogel will act as a "plug" to prevent reflux of liquid embolic such as Onyx 18 when it is injected through the catheter and out the distal end hole.

Each of the embodiments of the catheters of the present invention disclosed herein can have at least one "detachment" zone at a desired location. In such embodiments, the end of the catheter near the distal end hole may detach after injection of the liquid embolic agent, in certain circumstances, similar to the EV3/Medtronic Apollo detachable tip micro-catheter. In some embodiments, the wire extending in the distal segment may have a detachable segment. In some embodiments both the catheter and a wire may have at least one detachment zone, which when activated can effectively separate the distal end of the catheter and/or wire away from the more proximal segment.

In accordance with an aspect of the present invention, a catheter for delivering a liquid embolic agent to form a plug is provided, the catheter comprising a) an elongated tube having a lumen extending therethrough and a distal hole in communication with the lumen; b) at least one side hole positioned proximal of the distal hole and in communication with the lumen; c) a proximal hole in communication with the lumen through which the liquid embolic agent is injected; d) a proximal segment positioned proximal of the distal hole, the proximal hole positioned in the proximal segment; e) a distal segment, the distal hole positioned in the distal segment; and f) a flow restricting structure to temporarily block flow of the liquid embolic agent out the distal end hole to direct flow of the liquid embolic agent through the at least one side hole.

In some embodiments, the flow restricting structure temporarily restricts flow through a portion of the lumen distal of the side hole for formation of the plug from the liquid embolic agent adjacent the at least one side hole and proximal of the distal end hole.

In some embodiments, the catheter has a detachment zone proximal to the distal end hole for detaching the distal segment from the proximal segment after formation of the plug, the distal segment being left in a body of a patient. In some embodiments, the side hole(s) is in the detached distal segment.

In some embodiments, the flow restricting structure comprises a valve, the valve positioned distal of the at least one side hole. The valve in some embodiments automatically opens upon buildup of a predetermined pressure when the embolic agent exiting the side hole hardens to block flow through the side hole.

In some embodiments, the flow restricting structure includes a reduced inner diameter of the catheter or lumen distal of the at least one side hole to restrict flow distal of the at least one side hole.

In some embodiments, the flow restricting structure includes a wire extending distal of the at least one side hole to restrict flow distal of the at least one side hole. The wire can be removable to enable flow through the distal end hole after the plug is formed adjacent the at least one side hole or alternatively the wire can have a detachment zone detachable along with the distal segment of the catheter to separate a distal portion of the wire from a proximal portion of the wire. In some embodiments, this detached wire segment may be pushed out of the catheter by injecting additional liquid embolic, once a certain pressure is built up by the proximal plug forming and/or hardening, such that when the segment of wire or a similar coil is ejected, the distal catheter lumen will be free of obstruction and additional push of liquid embolic out of the distal end hole can proceed, until a desired lesion penetration is achieved.

In some embodiments, the flow restricting structure includes a coil positioned distal of the at least one side hole to restrict flow distal of the at least one side hole. The coil can be ejected from the catheter when a sufficient pressure of the embolic agent within the lumen is reached or alternatively the coil remains within the distal segment when detached from the proximal segment and in such embodiment the coil can be composed of a non-dissolvable or a dissolvable material.

In accordance with another aspect of the present invention, a catheter for delivering a liquid embolic agent to form a plug is provided, the catheter comprising a) an elongated tube having a lumen extending therethrough and a distal end hole in communication with the lumen; b) a flap formed in an outer wall of the elongated tube covering a side hole; c) a proximal hole in communication with the lumen through which the liquid embolic agent is injected; d) a proximal segment positioned proximal of the distal end hole, the proximal hole positioned in the proximal segment; and e) a distal segment, the flap positioned in the distal segment proximal of the distal end hole, wherein the flap is openable to enable outflow of the liquid embolic agent to form a plug adjacent the flap when the agent solidifies. A plurality of flaps for covering a plurality of side holes can also be provided, with one or more flaps covering each side hole.

In some embodiments, the catheter includes a flow restricting structure to temporarily block flow of the liquid embolic agent out the distal end hole and direct flow of the liquid embolic agent through the flap.

In some embodiments, the catheter has a detachment zone proximal to the distal end hole for detaching the distal segment from the proximal segment after formation of the plug, the distal segment being left in a body of a patient. In some embodiments, the flap is in the distal segment.

In accordance with another aspect of the present invention, a catheter for delivering a liquid embolic agent to form a plug is provided comprising a) an elongated tube having a lumen extending therethrough and a distal end hole in communication with the lumen; b) at least one side hole formable in a side wall of the elongated tube proximal of the distal end hole and in communication with the lumen; c) a proximal hole in communication with the lumen through which the liquid embolic agent is injected; d) a proximal segment, the proximal hole positioned in the proximal segment; e) a distal segment, the distal end hole positioned in the distal segment; and f) a detachment zone proximal to the distal end hole for detaching the distal segment from the proximal segment after formation of the plug, wherein the catheter includes a region composed of a material non compatible with a solvent such as DMSO or DSW, the region openable via dissolving the wall segment with the solvent infusion to enable outflow of the liquid embolic agent through the side wall of the elongated tube, to enable outflow of liquid embolic agent to form a plug adjacent the flap when the agent solidifies. Once the plug is formed the newly formed hole will be effectively blocked by the plug, and injection of liquid embolic can continue as desired out the distal end hole. The region can also be composed of material that is non-compatible with liquids or solvents other than DMSO for dissolving of the region upon infusion. The solvent utilized in some embodiments is a solvent to help prevent the liquid embolic agent from hardening within the catheter.

In some embodiments, the catheter includes a flow restricting structure to temporarily block flow of the liquid embolic agent out the distal end hole and direct flow of the liquid embolic agent through the newly formed side hole In some embodiments, the catheter has a detachment zone proximal to the distal end hole for detaching the distal segment from the proximal segment after formation of the plug, the distal segment being left in a body of a patient. In some embodiments, the non-DMSO compatible region is in the distal segment.

The catheter can similarly have a dissolvable region of a different material and different solvent to form a side hole. The dissolvable region can be dissolved by appropriate fluid solvent infusion in the catheter.

Various combinations of features described in the various embodiments herein are contemplated as well.

In accordance with another aspect of the present invention, a method for injecting a liquid embolic agent utilizing a plug and push technique is provided comprising the steps of;
  a) inserting into a vessel of a patient a catheter having a proximal hole, a distal end hole, a side hole proximal of the distal end hole and a lumen communicating with the proximal hole, distal end hole and the side hole, the distal end hole located at a distal segment of the catheter, the distal segment positioned distal of a proximal segment of the catheter;
  b) injecting the liquid embolic agent through the lumen and out the side hole while a distal section of the lumen of said catheter is temporarily obstructed to block outflow of the liquid embolic agent through the distal end hole;
  c) continuing injection of the liquid embolic agent until a proximal plug is formed adjacent the side hole to provide a block for proximal reflux of the liquid embolic agent when subsequently injected from the distal end hole, the plug formed proximal of the distal end hole;
  d) reversing the temporary obstruction of the distal section of the lumen to open the distal section to flow of the embolic liquid agent; and
  e) injecting the liquid embolic agent through the lumen to exit the distal end hole into a target tissue until desired penetration of the target tissue is achieved, the plug blocking reflux of the liquid embolic agent.

In some embodiments, a detachment zone proximal of the side hole can be provided.

In accordance with another aspect of the present invention, a method for injecting a liquid embolic agent utilizing a plug and push technique is provided comprising the steps of
  a) inserting into a vessel of a patient a catheter having a proximal hole, a distal end hole, a side hole proximal of the distal end hole and a lumen communicating with the proximal hole, distal end hole and the side hole, the distal end hole located at a distal segment of the catheter, the distal segment positioned distal of a proximal segment of the catheter;
  b) injecting the liquid embolic agent through the lumen and out the side hole wherein the liquid embolic agent initially flows out of the side hole and not out of the distal end hole, the liquid embolic agent injected until a proximal plug is formed adjacent the side hole to provide a block for proximal flow of the liquid embolic agent when subsequently injected through the distal end hole; and
  c) after step (b), injecting the liquid embolic agent through the distal end hole, the plug formed proximal of the distal end hole blocking the proximal flow of the liquid embolic agent injected out the distal end hole.

In some embodiments, a detachment zone proximal of the side hole can be provided.

In accordance with another aspect of the present invention, a method for injecting a liquid embolic agent utilizing a plug and push technique is provided comprising the steps of:
  a) inserting into a vessel of a patient a catheter having a proximal hole and a distal end hole, the distal end hole located at a distal segment of the catheter, the distal segment positioned distal of a proximal segment of the catheter;
  b) injecting a liquid through the catheter and to a dissolvable portion of the catheter to thereby dissolve the dissolvable portion and form a side hole;
  c) after step (b), injecting the liquid embolic agent through the side hole until a proximal plug is formed adjacent the side hole to provide a block for proximal reflux of the liquid embolic agent when subsequently injected from the distal end hole, the plug formed proximal of the distal end hole; and
  d) after step (c), injecting the liquid embolic agent via the proximal hole through the lumen to exit the distal end hole into a target tissue until desired penetration of the target tissue is achieved, the plug blocking reflux of the liquid embolic agent.

In some embodiments, a detachment zone proximal of the side hole can be provided.

In accordance with another aspect of the present invention, a method for injecting a liquid embolic agent utilizing a plug and push technique is provided comprising the steps of:
  a) inserting into a vessel of a patient a catheter having a lumen, proximal hole and a distal end hole, the distal end hole located at a distal segment of the catheter, the distal segment positioned distal of a proximal segment of the catheter,
  b) injecting a liquid through the catheter and to a dissolvable portion of the catheter to thereby dissolve the dissolvable portion and form a side hole;
  c) after step (b), injecting the liquid embolic agent through the lumen while a distal section of the lumen of said catheter is temporarily obstructed to block outflow of the liquid embolic agent through the distal end hole until a proximal plug is formed adjacent the side hole to provide a block for proximal reflux of the liquid embolic agent when subsequently injected from the distal end hole, the plug formed proximal of the distal end hole; and
  d) after step (c), injecting the liquid embolic agent via the proximal hole through the lumen to exit the distal end hole into a target tissue until desired penetration of the target tissue is achieved, the plug blocking reflux of the liquid embolic agent.

In some embodiments, a detachment zone proximal of the side hole can be provided.

DETAILED DESCRIPTION OF THE DRAWINGS

So that those having ordinary skill in the art to which the subject invention appertains will more readily understand how to make and use the surgical apparatus disclosed herein, preferred embodiments thereof will be described in detail hereinbelow with reference to the drawings, wherein.

DETAILED DESCRIPTION OF THE INVENTION

Figure 1:
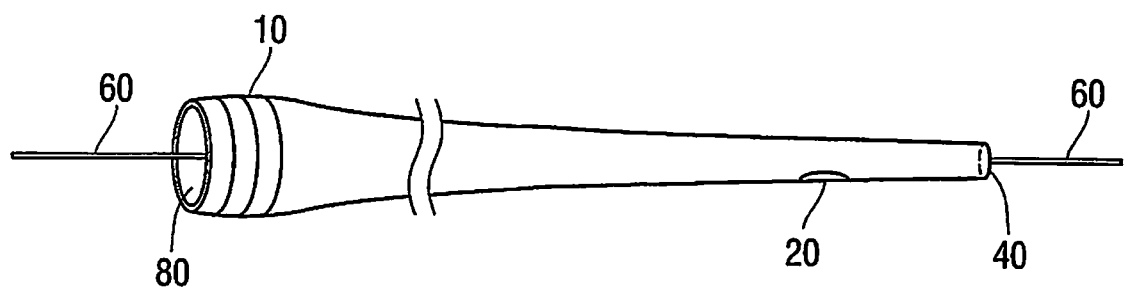
FIG. 1 is a side view of the single lumen catheter of one embodiment of the present invention.

The present invention provides catheters which improve the "plug and push" technique for application of liquid embolic agents to vessels where they solidify and embolize the vasculature. The present invention provides for liquid embolic agent delivery to the target site utilizing a catheter that provides initial injection proximal of the distal tip and distal hole of the catheter, where it provides a "block" or "plug" to prevent proximal flow along the catheter. This ensures that when the embolic agent is delivered to the target site, reflux of the agent along the catheter is prevented, thereby preventing flow into undesired areas and undesired vessels of the patient, which can result in serious risks. Various embodiments of the catheters of the present invention achieve this, and each is discussed in detail below.

Furthermore, preferred embodiments of the catheters of the present invention have a detachment zone which enables the catheter to be separated after use, leaving the distal tip of the catheter in the body. This is advantageous since due to the solidified embolic agent around the distal tip of the catheter, it is sometimes difficult to remove the catheter from the body and the tip of the catheter can get stuck. These embodiments are also discussed in detail below.

Further, some embodiments of the catheter of the present invention have structure or component(s) to initially block or restrict flow through the distal end hole and "encourage"

flow through the one or more side hole(s) which is proximal of the distal end hole. This facilitates initial flow only or mainly through the side hole(s). Various ways/structures to achieve this are discussed in detail below.

Still further, in some embodiments, the catheter ensures that a more viscous embolic agent is initially inserted proximal of the distalmost tip of the catheter, and allowed to solidify to form the plug, followed by injection of a less viscous embolic agent at the distalmost tip of the catheter.

The catheters of the present invention can be used in performing various medical procedures, such as the treatment of brain arteriovenous malformations via endovascular embolization.

The catheters of the present invention more safely and more effectively effect endovascular treatment of arteriovenous malformations and arteriovenous fistulas, reducing procedural times and exposure to X-ray radiation to the patient and the treating staff. The catheters provide embolic agent delivery systems that are easier to use, allow faster plug formation, require less procedural time and X-ray/radiation dosage, and are more consistently effective. They are effective in embolizations for treatment of other maladies as well.

The present invention is some embodiments uses a hole on the side of a single-lumen micro-catheter (hereinafter "side hole"), communicating with a lumen extending through the catheter, for preparing a plug. Alternatively, there may be multiple circumferential side holes disposed about the same segment of the catheter communicating with the lumen for preparing the plug. Preferably, a single lumen communicates with the side holes, although it is also contemplated that more than one lumen can be provided for flow of the embolic agent, communicating with different side holes.

As used herein the terms "proximal" and "distal" refer to the direction of catheter insertion such that "proximal" refers to the portion of the catheter closer to the user and "distal" refers to the portion of the catheter further from the user. Proximal and distal can also be used to refer to direction of blood flow, so that blood flows from proximal to distal.

As used herein, in embodiments that contain a detachment site, the term "proximal catheter segment" is proximal of the detachment site and the term "distal catheter segment" is distal of the detachment site such that the distal segment remains in the body and the proximal segment is withdrawn from the body, "Flow control" in the present disclosure is used to reduce flow of blood in the vessel. Flow control can encompass various techniques, including without limitation, a proximal balloon, a proximal plug of any sort, lowering blood pressure, temporary cardioplegia, and other modalities.

Referring now to the drawings and particular embodiments of the present disclosure, wherein like reference numerals identify similar structural features of the devices disclosed herein, there are illustrated several embodiments of the catheters of the present invention. Turning first to FIG. 1, one embodiment of the catheter of the present invention is shown. Catheter 10 of FIG. 1 depicts the most basic version of the catheter, which is untapered both internally and externally, has a single side hole, and no flow restricting structure e.g., no governing element or valve.

The proximal portion of catheter 10 has a proximal end hole 80, and the distal portion includes a side hole 20 to build a plug proximal to the distal-most end hole 40 of the catheter 10. The plug, when successfully deployed/formed by injection of an embolic agent through the side hole, prevents unwanted reflux of Onyx (or other similar or equivalent liquid embolic agent), and facilitates better distal penetration of the lesion during subsequent injection of the embolic agent through the distal end hole 40 after the plug is formed. If there is unwanted proximal reflux, there can be flow of embolic material into normal branches more proximally, which can result in unwanted occlusion of the branch, tissue ischemia, disability and/or death. The prevention of unwanted proximal flow therefore ameliorates possible unwanted occlusions of normal vessels.

With continued reference to FIG. 1, side hole 20 is positioned proximally of distal end hole 40. Although one side hole is shown, it is contemplated that multiple side holes can be provided. The side holes can be radially spaced and/or axially spaced to provide multiple exit openings for the agent. The one or more side holes communicate with a lumen, preferably a central lumen, within the catheter, and in the embodiment of FIG. 1, the catheter has only a single lumen for agent injection. However, it is also contemplated that the catheter can include more than one lumen for agent injection (e.g., different lumens for injection through the side hole and distal end hole, and/or different lumens for injection through different side holes) or for other uses.

Note that multiple side holes and/or multiple lumens can also be provided in the other embodiments of the catheters described herein.

Note the proximal hole in catheter 10, as well as in the other embodiments of the catheters disclosed herein, can be at the proximalmost end, aligned with the longitudinal axis of the catheter. Alternatively, it could be formed in a side wall or a side port of the catheter for embolic agent injection. Likewise, the distal end hole is shown at the distalmost end of the catheter, aligned with the longitudinal axis, but alternatively, in any of the embodiments disclosed herein, could be formed in a side wall of the catheter.

Catheter 10 has a removable wire 60 extending through the lumen, and preferably exiting the proximal end of the catheter.

The wire 60 in some embodiments is dimensioned to temporarily plug the distal end hole 40 or at least plug a region of the lumen distal of the side hole. Thus the wire 60 can provide a flow blocking or flow restricting structure to direct, e.g., encourage, flow of the embolic agent through the side hole when desired. In embodiments, e.g., where the catheter lumen is untapered, the wire itself can have a larger dimension, e.g., larger diameter, at a distal segment to restrict flow.

Figure 1A:
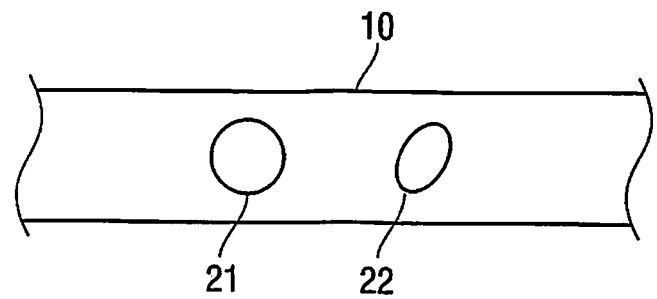
FIG. 1A is a partial view of the catheter of the present invention showing examples of two different shaped side holes which can be provided.

Referring now to FIG. 1A, side hole 20 may be perpendicular to catheter 10, such as depicted as side hole 21, or side hole 20 may be angled with respect to the longitudinal axis of catheter 10, such as depicted by angled side hole 22. Other shapes and orientations of the side holes are also contemplated. The side hole(s) in some embodiments can be flush with an outer surface of the elongated tube.

Figure 2:
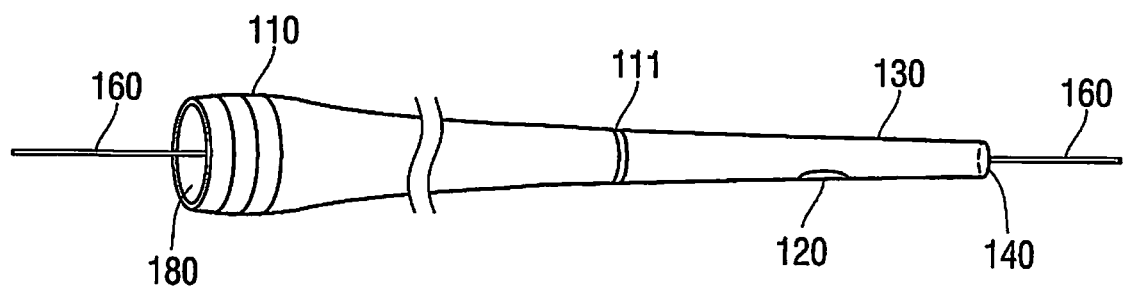
FIG. 2 is a side view of an alternate embodiment of the catheter of the present invention, the catheter having a detachment (breakaway) element near the proximal side of the side hole and further having a microwire extending through the detachment element, the catheter shown in the coupled state (condition)

FIG. 2 shows the catheter of FIG. 1 with the addition of a detachment (or breakaway) element 111 between the proximal end hole 180 and side hole 120 and tapered distal portion 130 of catheter 110. That is, the detachment element or detachment point or detachment region 111 is distal of the proximal end hole and proximal of the side hole 120. The detachment element 111 enables the proximal region (or proximal segment) of the catheter, which is axially spaced from the solidified embolic agent around the catheter, to be separated from the distal region (or distal segment) of the catheter 110 and removed from the patient's body if the distal segment is "stuck" in the vessel due to the solidified agent. The detachment element 111 can be just proximal to the side hole or further proximal of the side hole. Preferably, it is closer to the distal end of the catheter so the least amount of the catheter material remains in the body.

In some embodiments, the distal section of the catheter that is left behind in the body when the proximal section is separated and removed can be composed of absorbable material so it is absorbed by the body over time. Alternatively, it can be composed of material that does not absorb/resorb. Note such non-absorbable or absorbable materials for the distal end or tip of the catheter can be utilized for any of the catheters disclosed herein.

Figure 2A:
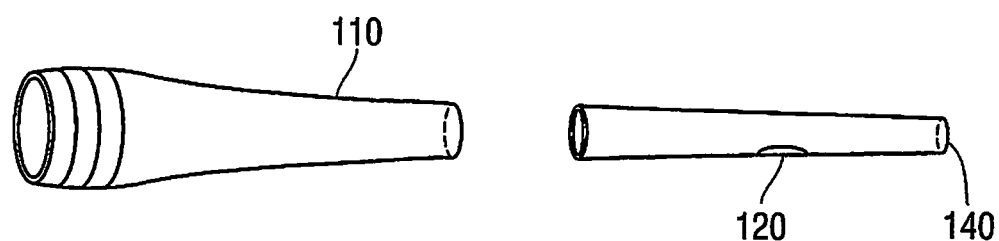
FIG. 2A is a side view similar to FIG. 2 showing the catheter of FIG. 2 in the uncoupled state (condition)

Detachment element 111 in FIG. 2 or in any of the embodiments disclosed herein may be a coupling, a score, a stressed area, or any other suitable structure for detaching the distal end of catheter 110 using a force, e.g., a perpendicular force, provided at the proximal end of the catheter 110. Other forms of detachment such as electrolytic, hydrostatic, thermal, and others are also contemplated. FIG. 2A illustrates the decoupling of the proximal and distal sections, showing the sections separated. In the next step (not shown) the separated proximal segment is removed from the patient's body. Note in this embodiment, wire 60 is also removed from the body.

Note the detachment preferably separates a majority of the catheter (the proximal segment) from the distal segment leaving the distal segment having the side hole and only a small segment of the distal portion of the catheter in the vessel, and the proximal segment is removed. That is, the proximal segment of the catheter, which is defined herein as the portion removed, preferably comprises the majority of the catheter length. The proximal and distal segments can also be considered herein as "first" and "second" segments, respectively.

The outer surface of the catheter 100 can in some embodiments be entirely smooth along its length so there are no bumps or other projecting surfaces or obstructions along its length. Such smooth surface can also be provided on the other catheters disclosed herein. The catheter 110 also has a distal tapered region forming a reduced diameter, but non-tapered distal regions are also contemplated. Such tapered/reduced diameter or non-tapered/unchanging diameter regions can be provided in the other catheters disclosed herein.

In some embodiments, the catheters of the present invention have a larger inner diameter until the end of the side hole, approximately 0.011 in for example and smaller thereafter, approximately 0.008 in for example. Other dimensions are also contemplated. In such embodiments, a wire like wire 160 of FIG. 2 can be provided. The wire can have an outer diameter of approximately 0.008 in for example to match the smaller inner diameter of the catheter lumen distal of the side hole. In this manner, initial injections of the embolic agent with the approximately 0.008 in. "blocking" wire in place allows the Onyx or other embolic fluid to "fill" that segment of the vessel at the side hole as it flows out the side hole, forming the "plug"; while the wire will completely obstruct injection through the inner lumen distal of the side hole to block flow out the distal end hole. Thus, as the embolic agent, e.g. Onyx 34, is injected, it does not flow out of the distal end hole, but only the side hole(s), preventing obstruction of the distal tip of the micro-catheter from stagnant Onyx that would otherwise be contained in it, and preventing egress of Onyx out the distal end hole before desired. Note the wire forms one type of blocking (flow restricting) structure to initially prevent flow out the distal end hole, i.e., encouraging flow out the distal end hole. Although the wire is described as having a matching dimension of the inner diameter of the catheter, it can be slightly smaller which would still limit the outflow of the agent through the distal end hole when the wire is present. Alternatively, the inner diameter of the catheter can be constant, and a distal segment of the wire can have a larger outer diameter to provide a blocking structure for the distal end hole. Other ways to direct or encourage flow through the side hole instead of the distal end hole are discussed below.

Note the wire can be withdrawn from the catheter in its entirety or alternatively have a breakaway portion, as discussed below, for separating the proximal section from the distal section either prior to injection through the side hole or after injection through the side hole. The breakaway portion can include a coupling, a score, a stressed area or other weakened portion to facilitating breaking/separating the distal section of the wire. It can also include a detachment mechanism using mechanical, thermal, hydrostatic, electrolytic or other types/forms of detachment.

In the basic embodiment, if less than two minutes are allowed from initial "plug" injection until subsequent "push" injections, the Onyx in the distal tip of the catheter would not normally precipitate fully, and thus does not obstruct the catheter. But if longer times are needed to form a proper "plug", the distal end hole could become obstructed.

In another alternative, the wire and/or catheter can be of constant diameters throughout, and the wire can have a detachment zone so that a distal segment of the wire, or a "coil", can be detached and left in the distal segment of the catheter, distal to the side hole. The proximal wire section can then be removed, and the distal wire section will significantly obstruct flow beyond the side hole and out of the distal end hole until a sufficient plug has been formed and somewhat hardened around the side hole, which would thereby significantly obstruct further flow out of the side hole. This obstruction of the side hole would result in slightly higher-pressure injections resulting in pushing out the distal and now disconnected wire or coil from the distal section of the lumen, and then additional liquid embolic can be injected out the now open lumen and distal end hole as desired to penetrate a desired lesion being embolized, while the plug already formed prevents reflux of embolic material proximally. In the latter scenario, the catheter may optionally be filled with an appropriate liquid embolic solvent prior to initial wire insertion or after wire insertion. Non-limiting examples of such solvents can include DMSO or D5W or others.

In some embodiments, the wire can then be removed from the lumen after the initial injection through the side holes thereby subsequently allowing flow out the tip.

In alternate embodiments where the distal end of the wire is left in the body, the wire can be composed of a dissolvable or absorbable material.

Note in the embodiments utilizing a detachable wire, the distal end of the wire can be detached independent of the detachment of the distal end of the catheter.

Figure 8:
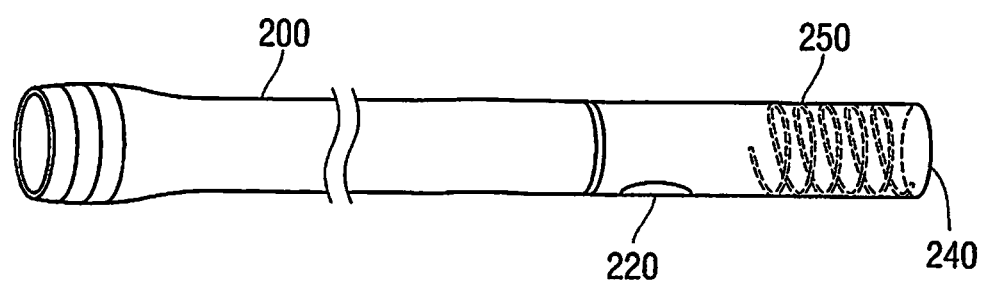
FIG. 8 is a side view of an alternate embodiment of the catheter of the present invention having a detached coil in the distal segment, with the coil pusher wire removed.

In an alternate embodiment, a coil can be provided as a blocker (flow blocking structure/flow restricting structure) positioned distal of the side hole to direct, i.e., encourage, flow through the side hole. As shown in FIG. 8, the coil 250 is positioned within the lumen of the catheter 200, between the side hole 220 and distal end hole 240, to either completely, or partially, block the lumen until enough embolic agent has exited the side hole 220 and created the plug around the catheter 200. The coil 250 in one embodiment is removed from the catheter 200 after injection of the embolic agent through the side hole 220 to open the lumen distal of the side hole 220 for injection of embolic agent through the distal end hole 240.

In other embodiments, the coil 250 is configured to block flow of the more viscous embolic agent (for formation of the plug adjacent the side hole) but enable flow of the less viscous agent through the coil subsequent to the outflow of the more viscous agent through the side hole to form the plug. In such embodiments, the coil does not need to be removed after injection through the side hole since the less viscous agent can flow through the coil and out the distal hole. Alternatively, the coil can be withdrawn after injection through the distal end hole, or alternatively, be detachable and left in the body when the distal section of the catheter is detached as described herein. Alternatively, in such embodiments, the coil can be detachable and ejected out the distal end hole when enough pressure is built up during injection, or alternatively, be detachable and left in the body when the distal section of the catheter is detached as described herein. That is, in such embodiments, once the proximal plug is formed adjacent the side hole and obstructing the side hole, and the agent is injected through the distal hole, the coil can be ejected distally out of the catheter and left in the body or, in some embodiments, remain within the distal segment of the catheter, which will sometimes remain in the body when it is detached.

In some embodiments, the coil can be composed of a plastic or other material that is dissolved by DMSO (or other liquids). The coil can obstruct flow in the distal segment beyond the side hole and the distal end hole until the coil is dissolved. That is, the coil, or other blocking structures described herein, could be a DMSO (or other liquid) dissolvable plug which would block the lumen distal of the side hole until it is dissolved by infusion of DMSO (or other liquid). In other embodiments, the coil can be made of an absorbable material and left in the body.

In alternate embodiments, as mentioned above, the coil which is positioned between the side hole and distal end hole, is ejected from the catheter. That is, once an adequate plug is formed via flow of embolic agent through the side hole and allowed to harden, exit of additional liquid embolic through the side hole becomes blocked, and then pressure in the catheter builds up upon further injection causing ejection of the coil from the catheter through the distal end hole, allowing further liquid embolic agent to be injected and flow out the end hole and penetrate the target lesion.

In an alternate embodiment, the catheter has at least one dissolvable region that can comprise a side hole (or multiple side holes) when said solvent is infused and dissolves the structure of the at least one region. The solvent used can be DMSO or other solvent or liquid which helps to prevent Onyx or other liquid embolics from hardening within the catheter, or the solvent can be an altogether different solvent. More specifically, the catheter can have select regions not compatible with DMSO or not compatible with a different select solvent which are intended to form side holes. Thus, prior to DMSO (or other solvent or liquid) injection, the catheter is devoid of side holes. When the DMSO (or other solvent or liquid) is injected, the non-compatible portions dissolve to form (create) one or more side holes in vivo. Note other solvents or liquids can be used to dissolve the select regions of the catheter. It is also contemplated that the distal end hole or part or all of the distal segment inner lumen can be formed by a dissolvable region of the catheter, thus the end hole or part or all of the distal segment inner lumen remaining closed until desired.

Figure 3:
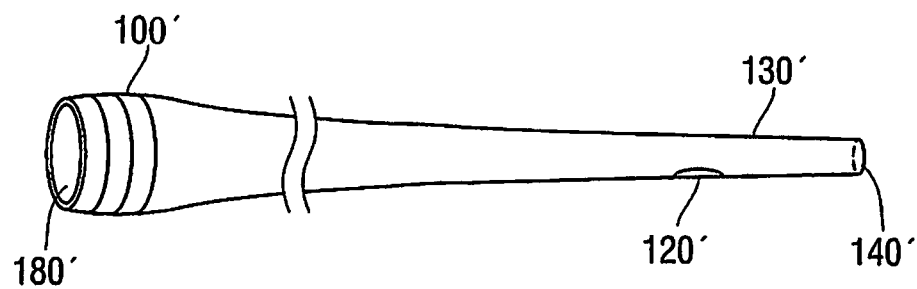
FIG. 3 is a side view of an alternate embodiment of the catheter of the present invention without the microwire of FIG. 2.

FIG. 3 illustrates an embodiment of the catheter similar to FIG. 2 except a wire 160 is not provided. Catheter 100' of FIG. 3 is similar to catheter 100 of FIG. 2 as it has a single central lumen, a proximal hole 180', a side hole 120' and a distal end hole 140' in distal portion 130'. The distal end of catheter 100' is tapered along region 130'. The catheter is illustrated in which a single lumen is provided and the catheter does not have a balloon so no balloon prep is necessary. The catheter as noted above, differs from that of FIG. 2 since it does not have a wire like wire 160 to block flow, however, other structure to block the lumen distal of the side hole can be provided, such as the other structures described herein.

Figure 3A:
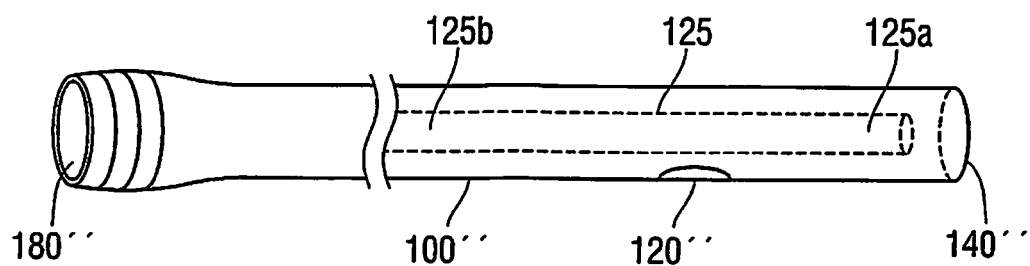
FIG. 3A is a side view of an alternate embodiment of the catheter of the present invention having a lumen with an inner diameter smaller distal to the side hole.

For example, the catheter 100' can have a small channel that is formed at the end of the single lumen that is configured to limit flow of certain materials. In some embodiments, the smaller channel allows air, saline, heparinized saline, diluted contrast and DMSO to exit but does not allow pure contrast to exit. It can also be dimensioned to allow dimethyl sulfoxide (DMSO) or less viscous Onyx, such as Onyx 18 (or other fluids/materials of similar or lower viscosity) to flow through, but not allow more viscous Onyx 34 (or other more viscous fluids/materials) to flow through. In this manner, the more viscous material, e.g. Onyx 34, would instead flow out of the side hole since it could not flow through the small channel distal of the side hole. Thus, the small channel provides a blocking or restricting structure to limit flow distal of the side hole and direct it through the side hole. In other words, in this embodiment, this catheter uses a particular size/diameter and shape of a channel distal to the side hole that would allow passage of DMSO, and would allow passage of the less viscous embolic agent such as ONYX 18, but would not allow passage of Onyx 34 or the like. Various internal membranes may, in some embodiments, be used, placed in the lumen to restrict flow, which may also have a valve or flap function to open for passage of a wire, coil, or other structures in some embodiments. The reduced diameter channel could be formed by a taper in the distal region of the catheter, distal of the side hole 120', as shown in FIG. 3. Alternatively, the reduced diameter channel can be formed by altering the size of the internal lumen 125, whether a taper or no taper is provided in the outer diameter of the catheter, as shown for example in the non-tapered catheter 100" of FIG. 3A, wherein region 125*a* of lumen 125 between side hole 120" and distal end hole 140" has a smaller diameter than more proximal region 125*b* of lumen 125 (which can be due in some embodiments to a change in thickness of the catheter wall). That is, the inner diameter can be greater in the proximal region than in the distal region (distal of the side hole). Such changing diameters in the catheter OD and/or ID, and/or or changes in the ID of the lumen) can be utilized in any of the embodiments of the catheter disclosed herein.

As incorporated into the present invention, the foregoing is not dependent upon particle size. The difference between Onyx 34 and Onyx 18 is not related to particle size, but rather the concentration of the suspended material (8% vs. 6%). Thus, the concentration results in different viscosity, but does not differ in particle size, in the various formulations of precipitating hydrophobic injectable liquid. Nonetheless, other embodiments that utilize particle size differences may be employed as well; optionally employing different embolic materials. In this manner, the smaller channel would restrict materials of a particle size larger than a predetermined size, e.g., a diameter of the channel/lumen.

Figure 4:
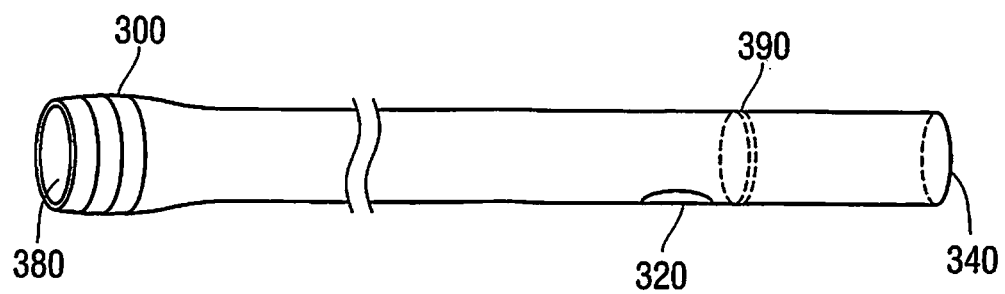
FIG. 4 is a side view of an alternate embodiment of the catheter of the present invention having a blocking structure proximal to the distal hole and distal of the side hole.

Referring now to FIG. 4, another embodiment of the catheter of the present invention is illustrated. Catheter 300 has a side hole 320, a distal end hole 340, a proximal hole 380, and a blocking or governing element. In this embodiment, the blocking element (structure) is in the form of a flap valve 390, or alternatively, a "push" diaphragm, or other device capable of stopping embolic agent flow from deploying out of the distal end hole 340. Thus, the flap valve 390 forms a blocking (restricting) structure to divert flow to side hole 320. The valve 390 can be positioned anywhere between the side hole 320 and distal end hole 390, but preferably is positioned immediately distal to the distal end of the side hole 320 to prevent flow within the lumen of catheter 310 distal of the side hole 320. Catheter 300 may alternatively incorporate the design of the Strata® valve, or other type of valve, which may have magnetic, electric current, or other inputs to open or close.

The valve 390 (or other type of valve) can be opened or closed by various mechanisms, such as mechanically by attachment of a wire or elongated member to the valve so the user can selectively manipulate the wire or elongated member to open and close the valve. Alternatively, the valve can be closed by a magnetic field created by an electric current applied after infusion of dimethyl sulfoxide. That is, the valve can be opened by removal of the electric current (after the Onyx 34 or similar is injected and an adequate proximal "plug" is created). In particular, the valve can contain a magnet or other structure or elements inside the valve mechanism that allows the practitioner to change the opening setting of the valve as desired during a procedure.

Alternatively, non-magnetic micro-valve technology may be employed. For example, a solenoid micro-valve may be utilized. The solenoid micro-valve uses a coil of wire wound in a helix, like a compressed spring. A magnetic field is created by passing current through the solenoid. The placement of a metallic object within the coil and the ability to vary the current, allows the object to move. In short, a solenoid micro-valve is simply a solenoid with an actuator inside of it. The actuator is situated above the channel of a micro-fluidic device and pushes down on the ceiling of the channel to collapse it and obstruct its flow. Valves opened and closed by other compatible mechanisms can be used as well.

In some embodiments the valve automatically opens if a certain amount of pressure is applied. That is, the embolic agent initially exits the side hole until the pressure builds to a predetermined amount as the side hole becomes blocked, then the pressure forces open the valve so the agent can be injected through the lumen past the side hole and out the distal end hole. Note the valve in some embodiments is configured so that the delivery wire, if utilized, can pass through the valve without affecting its function. In these embodiments, the valve would be configured so it would easily allow the wire to pass through, otherwise if it blocked passage, the wire could undesirably exit the side hole rather than the distal hole, in embodiments that have one or more preformed side hole(s). In preferred embodiments the valve is also configured so as not to significantly increase the stiffness or bulkiness of the catheter which could adversely affect delivery.

The valve can be semi-permeable, selectively permeable, or non-permeable. The valve can be fixed and not able to open if composed of a selectively permeable or semipermeable material for exit of certain materials, or materials of certain viscosity, through the valve. Alternatively, the valve can open in response to pressure, magnetic field, or a combination thereof, and/or other triggers, or by user manipulation as described above. In alternative embodiments, the valve may be opened by a certain fluid pressure and/or passage of a wire therethrough, and/or various combinations.

Figure 4A:
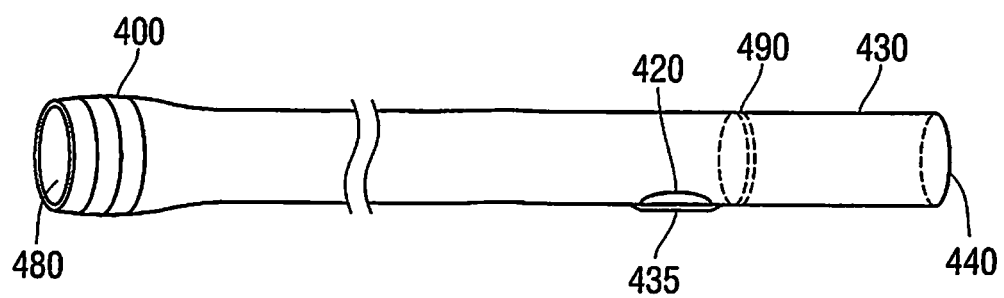
FIG. 4A is a side view of an alternate embodiment of the catheter of the present invention having a blocking structure proximal to the distal hole and distal of the side hole and a flap covering the side hole.

In some embodiments, the side hole of the catheter can be covered by a flap or a valve that can be opened by a certain fluid pressure or by other methods such as described above. For example, as shown in FIG. 4A, catheter 400 has a valve 490 in the catheter lumen distal of the side hole 420 and a second valve/flap 435 is positioned over side hole 420 to cover side hole 420. The flap 435 can be on an internal side or an external side of the side hole 420, and can be flush with the catheter wall. This can allow infusion of a solvent with a wire in place, or under sufficient pressure to open the valve 490, in order to fill the entire catheter lumen with the solvent. Subsequent initial injection of a liquid embolic can then be performed without a wire crossing the inner valve/flap 490, and under sufficient pressure to open only the side hole valve/flap 435, but not sufficient pressure to open said inner luminal valve/flap 490. This would result in initial injections of liquid embolic only out of said side hole 420 to create an optimal proximal plug. Once a sufficient proximal plug is formed and partially hardened, the plug will also increase resistance to flow out of said side hole 420. Thereafter, liquid embolic can be injected under higher pressures, opening the inner luminal valve 490, and allowing flow of liquid embolic through the distal catheter segment 430, distal to said side hole 420, and out the distal end hole 440. Injection can then be continued until desired penetration of a lesion is achieved. Thus, in some embodiments, the valves can be configured to open at different pressures to direct desired flow out the side hole or distal end hole.

As noted above, the valve utilized optimally will not affect delivery of the microcatheter. That is, the valve optimally would not stiffen or add bulkiness to the catheter too much as to make it harder to deliver. The valve is optimally designed to enable a wire to be inserted therethrough. If too stiff, the wire could be blocked and exit the side hole instead, or be blocked entirely.

As noted above, in one embodiment, the catheter is manufactured without side hole(s) and relies on the DMSO (or other liquid or solvent) to dissolve the catheter to form the side hole(s). In alternative embodiments, the catheter can be manufactured with one or more side holes that are covered by other material forming covers or flaps which are dissolvable by the liquid or solvent in order to open (expose) the side holes.

Referring back to FIG. 4, exit through the side hole 320 is governed (restricted) by the use of a semi-permeable membrane flap (valve) across the diameter of the catheter at the distal end of side hole 320. The semi-permeable membrane can be a type of biological or synthetic, polymeric membrane that will only allow certain molecules or ions to pass through it by diffusion. In such embodiment, the flap may be used to block the lumen, preventing Onyx (or other embolic agent of a certain particle size or viscosity) from deploying through the distal hole 340 of catheter 300, thereby directing it through side hole 320. Alternatively, such flap can be placed over the distal end hole 340 to cover hole 340, either internally or externally of the distal end hole 340, to limit flow out the distal hole 340.

In particular, as shown in FIG. 4A, the flap 490 can be placed within the catheter 400 at the distal end of the side hole 435, such that a wire inserted through the lumen can push it aside, but it will revert to its original (closed) position when the wire is removed. In some embodiments, the flap is permeable to liquid dimethyl sulfoxide, but not to any Onyx, but once a certain pressure is built up from the plug obstructing the side hole, the pressure of the Onyx column will push the flap open, and allow distal flow of Onyx. In other embodiments, the valve is permeable only to particles of a sufficiently small size. In other embodiments, the side hole may be covered with a substance that is not compatible with the desired solvent e.g., DMSO, and infusion of the solvent will cause the side hole covering to dissolve in vivo, thereby opening the side hole. Other methods of opening a side hole cover may be employed as well.

As noted above, the side flap or side catheter segment could be non-DMSO compatible which dissolves and become side hole(s) only after placement at the target site and DMSO is infused through the lumen of the catheter.

The valve element 490 in some embodiments can utilize a bi-stable micro-valve such as in U.S. Pat. No. 6,663,821 or a similar valve. In some embodiments, the catheter employs a bi-stable micro-valve of shape memory material that is operatively connected to a micro-catheter at the distal end of side hole 435. The bi-stable micro-valve includes tips that can be closed off until the valve is in the desired position. Once it is in position, it can be opened and closed. The system can use heat and/or pressure to open and close the micro-valve 490.

Figure 5:
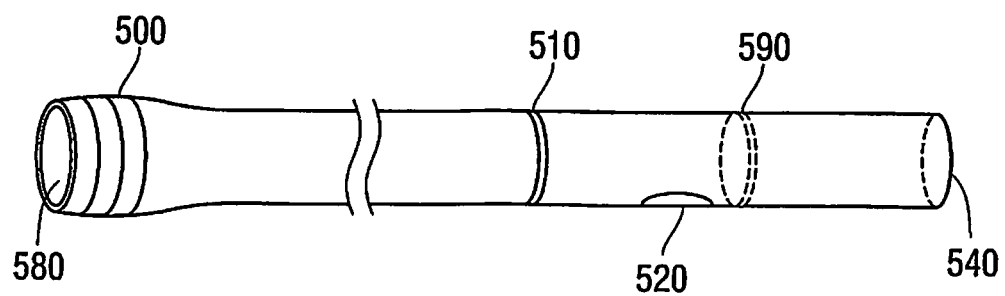
FIG. 5 is a side view of an alternate embodiment of the catheter of the present invention having a blocking structure and a detachment element proximal to the blocking structure.

The catheter of FIG. 5 is similar to the catheter of FIG. 4 except for the addition of a detachment element 510 between proximal end hole 580 and side hole 520. The detachment element 510 of catheter 500 can be the same as the detachment element as described above, optionally leaving the distal segment of catheter 500, which includes the segment containing the side hole 520 and distal end hole 540, in the patient as the proximal segment is removed.

It should be noted that the term "governing" as applied to the present invention, comprises a broad range of governing elements, generally distal to the proximal segment. These include anything that can open or close the connection (and flow) between the two segments, or block or limit/restrict flow in the distal segment, including for example a simple pressure valve, a valve with a different biocompatible solvent, a flap with at least one detachment zone, a controllable valve that can open and close as desired by the user, a wire obstruction element, a coil obstruction element, a separate-element detachable DMSO non-compatible detachable plug, etc.

Additionally, the catheters of the present invention can include a detachment element, being any element or device capable of making the distal tip of the catheter (the distal segment which includes the distal end hole and preferably the side hole(s) as well) separate from the proximal segment (the segment proximal of the distal segment).

Figure 6:
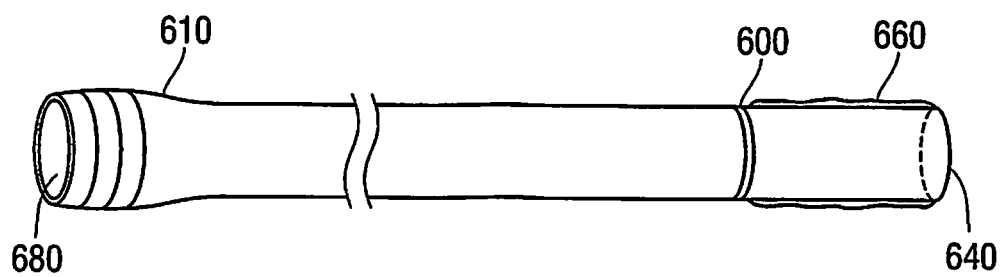
FIG. 6 is a side view of an alternate embodiment of the catheter of the present invention having a zone of hydrogel coated on the exterior surface proximal to the distal end of the catheter as an alternative to a side hole.

Referring now to FIG. 6, an alternate embodiment of the present invention is illustrated. Catheter 610 has an end hole 640, proximal hole 680 and a zone 660 of hydrogel coating the exterior circumference of catheter 610 proximal to end hole 640. In this embodiment, no side hole is required, although in some embodiments it can be included. Hydrogel zone 660 extends approximately 1 mm to approximately 3 cm from the distal end hole 640, and preferably extends approximately 3 mm to approximately 10 mm. from the end hole 640, although other zone lengths/coverage are also contemplated. There may be a gap between the end hole 640 and the hydrogel zone as well, which may be between approximately 0.1 mm and approximately 10 cm long, although gaps of other lengths are also contemplated. A detachment element 600 is shown proximal of the hydrogel zone 660. In use, the hydrogel can be allowed to swell in vivo, optionally with an additional stimulus. Once fully swollen, the hydrogel occludes the vessel along the hydrogel zone, thereby creating a "proximal plug" and preventing unwanted reflux of liquid embolic when the liquid embolic is injected through the catheter and out the distal end hole. That is, a zone of coating is provided on an exterior portion of the catheter 600, the coating swellable in vivo to block proximal flow of the liquid embolic agent when the liquid embolic agent is injected through the distal end hole. Other swellable materials can also be utilized.

Figure 7:
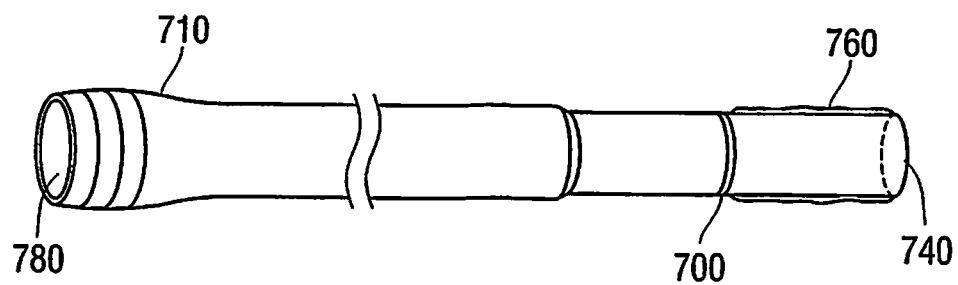
FIG. 7 is a side similar to FIG. 6, except the catheter includes a detachment element proximal to the zone of hydrogel.

The proximal segment can terminate in some embodiments in a detachment zone such as shown in the embodiment of FIG. 7. The distal segment of catheter 710 extends from the detachment zone 700 to the distal end hole 740, and the swellable coating 760 is configured so it does not obstruct the distal end hole 740. In this version, like catheter 600, the swellable coating e.g., hydrogel, becomes the plug so no side hole is needed. Once swelled to prevent reflux, the embolic agent can be injected through proximal hole 780 to flow through the catheter lumen and exit distal end hole 740. The detachment zone, as described above, enables the proximal segment to be separated from the distal segment if desired, leaving the distal segment in the body. In this embodiment, the hydrogel zone is distal of the detachment zone.

As an alternative, a balloon can be provided on the catheter inflatable to block reflux of the embolic agent. The inflatable balloon can be part of the catheter used to inject the agent i.e., attached to the catheters disclosed herein, or alternatively, can be part of an outer catheter which is positioned over the agent injection catheters disclosed herein. That is, one or more balloons can optionally be included and used proximally on the catheters disclosed herein or included on an external catheter through which the catheter of the present invention is advanced, to control blood flow and enhance the ability to form a plug at the exact desired location, without blood flow taking the liquid embolic further downstream.

The various embodiments of the catheters of the present invention may be used by employing one or more of the following methods.

For example, in one embodiment, a method for using the catheter for endovascular treatment of arteriovenous malformations and arteriovenous fistulas is provided comprising the steps of:

a) inserting a catheter with a side hole, a distal end hole and a governing (blocking or restricting) element in an open (flow-through) position, the governing element capable of opening and closing a distal portion of the lumen of the catheter which communicates with a more proximal portion;

b) advancing the catheter to a target vessel proximal to a target lesion;

c) injecting a liquid solvent into the catheter;

d) closing the governing element;

e) injecting a liquid agent, which exits the side hole, to form a plug around the side hole between a detachment zone (if present) of the catheter and the distal end hole;

f) stopping injection when the opening of the side hole is covered adequately with the liquid embolic agent and when the adjacent vessel lumen is obstructed by the plug;

g) waiting until the plug is at least partially solidified;

h) opening the governing element;

i) injecting additional liquid embolic agent (either the same agent or a different agent, e.g., an agent of a higher viscosity or a different particle size or a different material), until achieving desired penetration of the target lesion with the agent;

j) stopping injection when the optimal amount of the liquid embolic agent is present in the lesion; and k) removing the catheter from its proximal end, wherein if the catheter includes a detachment zone, the distal end of the catheter is detachable at the detachment zone of the catheter if sufficient force is required to remove the catheter.

It should be appreciated, that in the above method, the closing and opening of the governing element is user controlled, however, alternatively, the closing and opening of the governing element could occur automatically by the various methods disclosed herein.

In accordance with another method of using the catheter of the present invention for endovascular treatment of a lesion, the method includes a) inserting a catheter having a side hole, a proximal hole proximal of the side hole and a detachment zone distal of the proximal hole;

b) advancing the catheter to a target vessel proximal to a target lesion;

c) advancing a wire with a detachable distal tip, wherein the wire in some embodiments has a detachable length of a distance between the distal end of the side hole and the distal end-hole;

d) detaching the distal end of said wire and removing the wire by its proximal end, leaving the distal end of the wire in the catheter;

e) injecting a liquid solvent through the lumen of said catheter;

f) injecting a liquid embolic agent to form a plug around the side hole between said detachment zone (when present) and the distal end hole, the catheter lumen distal to the side hole being substantially obstructed by the detached distal wire, thereby obstructing flow of liquid embolic agent through the distal catheter segment and out the distal end hole;

g) waiting until the plug is partially solidified;

h) injecting additional liquid embolic agent (either the same or different agent from step (f)) with the plug at said side hole now having higher resistance then the wire in the distal catheter region, causing the additional liquid embolic injection to push out the detached wire segment through the end hole;

i) continuing liquid embolic injection until desired penetration of the target lesion is achieved;

j) stopping injection when an optimal amount of the liquid embolic is present in the lesion; and k) removing the catheter from its proximal end, wherein if the catheter includes a detachment zone, the distal end of the catheter is detachable at the detachment zone of the catheter if sufficient force is required to remove the catheter.

It should be appreciated that in the above method the wire is detachable, however in alternate embodiments disclosed herein it is non-detachable. Also, instead of a wire, a coil as described herein can be used in the above method.

Methods of using the various catheters disclosed herein for endovascular treatment to create a proximal plug for plug and push embolic agent delivery techniques are also contemplated, e.g., the catheters with swellable regions, dissolvable portions, flaps, etc. can be used for the aforedescribed embolic liquid agent injection methods Although the invention has been described in detail in the foregoing embodiments for the purpose of illustration, it is to be understood that such detail is solely for that purpose, and that variations can be made therein by those skilled in the art without departing from the spirit and scope of the invention, except as it may be described by the following claims.

Although the apparatus and methods of the subject invention have been described with respect to preferred embodiments, which constitute non-limiting examples, those skilled in the art will readily appreciate that changes and modifications may be made thereto without departing from the spirit and scope of the present invention as defined by the appended claims.

Additionally, persons skilled in the art will understand that the elements and features shown or described in connection with one embodiment may be combined with those of another embodiment without departing from the scope of the present invention and will appreciate further features and advantages of the presently disclosed subject matter based on the description provided.

Throughout the present invention, terms such as "approximately," "about", "generally," "substantially," and the like should be understood to allow for variations in any numerical range or concept with which they are associated. It is intended that the use of terms such as "approximately" and "generally" and "about" should be understood to encompass variations on the order of 25%, or to allow for manufacturing tolerances and/or deviations in design.

Although terms such as "first," "second," "third," etc., may be used herein to describe various operations, elements, components, regions, and/or sections, these operations, elements, components, regions, and/or sections should not be limited by the use of these terms in that these terms are used to distinguish one operation, element, component, region, or section from another. Thus, unless expressly stated otherwise, a first operation, element, component, region, or section could be termed a second operation, element, component, region, or section without departing from the scope of the present invention.

Each and every claim is incorporated as further disclosure into the specification and represents embodiments of the present disclosure. Also, the phrases "at least one of A, B, and C" and "A and/or B and/or C" should each be interpreted to include only A, only B, only C, or any combination of A, B, and C.

What is claimed is:

1. A catheter for delivering a liquid embolic agent to form a plug, the catheter comprising:
   an elongated tube having a lumen extending therethrough and a distal end hole in communication with the lumen;
   at least one side hole positioned proximal of the distal end hole and in communication with the lumen;
   a proximal hole in communication with the lumen through which the liquid embolic agent is injected;
   a proximal segment positioned proximal of the distal end hole, the proximal hole positioned in the proximal segment;
   a distal segment, the distal end hole positioned in the distal segment; and
   a flow restricting structure to temporarily block flow of the liquid embolic agent out the distal end hole and direct flow of the liquid embolic agent through the at least one side hole.

2. The catheter of claim 1, wherein the flow restricting structure temporarily restricts flow through a portion of the lumen distal of the at least one side hole for formation of the plug from the liquid embolic agent adjacent the at least one side hole and proximal of the distal end hole.

3. The catheter of claim 1, wherein the catheter has a detachment zone proximal to the distal end hole for detaching the distal segment from the proximal segment after formation of the plug for leaving the distal segment in a body of a patient.

4. The catheter of claim 1, wherein the flow restricting structure comprises a valve, the valve positioned distal of the at least one side hole.

5. The catheter of claim 4, wherein the valve automatically opens upon buildup of a predetermined pressure when the liquid embolic agent exiting the at least one side hole hardens to restrict flow through the at least one side hole.

6. The catheter of claim 1, wherein the flow restricting structure includes a reduced inner diameter distal of the at least one side hole to restrict flow distal of the at least one side hole.

7. The catheter of claim 1, wherein the flow restricting structure includes a wire extending distal of the at least one side hole to restrict flow distal of the at least one side hole.

8. The catheter of claim 7, wherein the wire is removable to enable flow through the distal end hole after the plug is formed adjacent the at least one side hole.

9. The catheter of claim 7, wherein the wire has a detachment zone detachable along with the distal segment of the catheter to separate a distal portion of the wire from a proximal portion of the wire.

10. The catheter of claim 1, wherein the flow restricting structure includes a coil positioned distal of the at least one side hole to restrict flow distal of the at least one side hole.

11. The catheter of claim 10, wherein the coil is ejected from the catheter when a sufficient pressure of the embolic agent within the lumen is reached.

12. The catheter of claim 10, wherein the coil remains within the distal segment of the catheter when the distal segment is detached from the proximal segment.

13. The catheter of claim 10, wherein the coil is composed of a dissolvable material.

14. The catheter of claim 1, wherein the catheter has an external surface, and the external surface is smooth along a length thereof.

15. The catheter of claim 1, wherein the distal segment has a channel configured to allow passage of air, contrast, saline, DMSO, and fluids with a lower viscosity than Onyx 34, but prevent passage of Onyx 34 and fluids with a similar or higher viscosity than Onyx 34.

16. The catheter of claim 1, wherein the at least one side hole is flush with an outer surface of said elongated tube.

17. A catheter for delivering a liquid embolic agent to form a plug, the catheter comprising:
   an elongated tube having a lumen extending therethrough and a distal end hole in communication with the lumen;
   at least one side hole formable proximal of the distal end hole for communication with the lumen;
   a proximal hole in communication with the lumen through which the liquid embolic agent is injected;
   a proximal segment, the proximal hole positioned in the proximal segment;
   a distal segment, the distal end hole positioned in the distal segment; and
   a detachment zone proximal to the distal end hole for detaching the distal segment from the proximal segment after formation of the plug;
   wherein the catheter includes a region composed of a material non compatible with a solvent injected into the lumen, the region openable by the solvent dissolving the region to form the at least one side hole to enable outflow of the liquid embolic agent through the at least one side hole in a side wall of the elongated tube.

18. The catheter of claim 17, further comprising a flow restricting structure to temporarily block flow of the liquid embolic agent out the distal end hole and direct flow of the liquid embolic agent through the side wall opened by the solvent.

19. The catheter of claim 18, wherein the flow restricting structure includes one or more of a valve, wire or coil in the lumen of the catheter distal of the region openable by the solvent.

* * * * *